United States Patent [19]

Hess et al.

[11] Patent Number: 4,575,240

[45] Date of Patent: Mar. 11, 1986

[54] VISIBLE SAMPLE CHAMBER FOR FLUID ANALYSIS

[75] Inventors: Craig N. Hess, Brookline; Robert S. Potts, Sherborn, both of Mass.

[73] Assignee: Corning Glass Works, Corning, N.Y.

[21] Appl. No.: 502,943

[22] Filed: Jun. 10, 1983

[51] Int. Cl.[4] .................. G01N 21/05; G01N 33/49
[52] U.S. Cl. ................................ 356/246; 356/39; 356/40
[58] Field of Search ................ 356/246, 42, 40, 39, 356/135, 137, 410, 411, 440; 250/576

[56] References Cited

U.S. PATENT DOCUMENTS

| | | | |
|---|---|---|---|
| 2,396,260 | 3/1946 | Gradisar et al. | 356/42 |
| 2,486,956 | 11/1949 | Lundberg | 356/42 |
| 2,780,131 | 2/1957 | Lanneau et al. | 356/246 X |
| 2,899,858 | 8/1959 | Stott | 356/246 X |
| 3,533,698 | 10/1970 | Brown et al. | 356/42 X |
| 3,902,807 | 9/1975 | Fleming et al. | 356/51 X |
| 4,014,611 | 3/1977 | Simpson et al. | 356/72 |
| 4,134,678 | 1/1979 | Brown et al. | 356/39 |
| 4,245,907 | 1/1981 | Rosen | 356/246 X |

*Primary Examiner*—Vincent P. McGraw
*Assistant Examiner*—Robert D. V. Thompson, III
*Attorney, Agent, or Firm*—W. J. Simmons, Jr.

[57] ABSTRACT

Disclosed is a sample chamber which is particularly adapted to the spectrophotometric analysis of blood samples. The instrument of which the sample chamber is a part includes means for directing a beam of light through the sample fluid and means for analyzing the light emanating from the fluid. The sample chamber comprises a first transparent member having a flat surface. A surface of a prism is disposed adjacent to the flat surface of the first member, and a resilient gasket located between the prism and the first member seals off a region which forms the sample chamber. A spring on a door, which closes to a position adjacent to the prism, engages the hypotenuse surface thereof to force the prism against the first member and compress the resilient gasket. First and second holes through the prism intersect the first surface thereof at opposite sides of the chamber formed by the gasket to enable the sample fluid to flow through the chamber.

5 Claims, 8 Drawing Figures

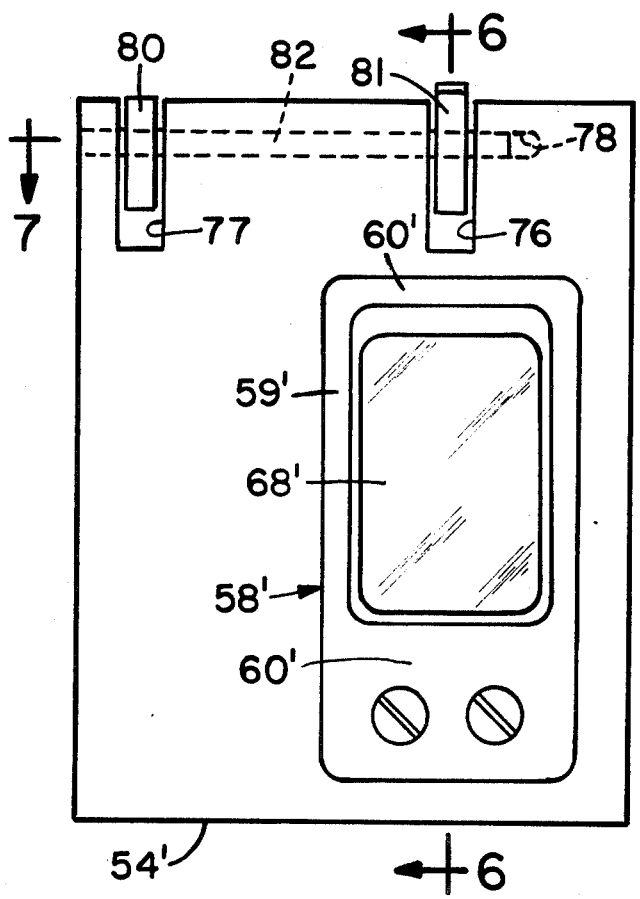
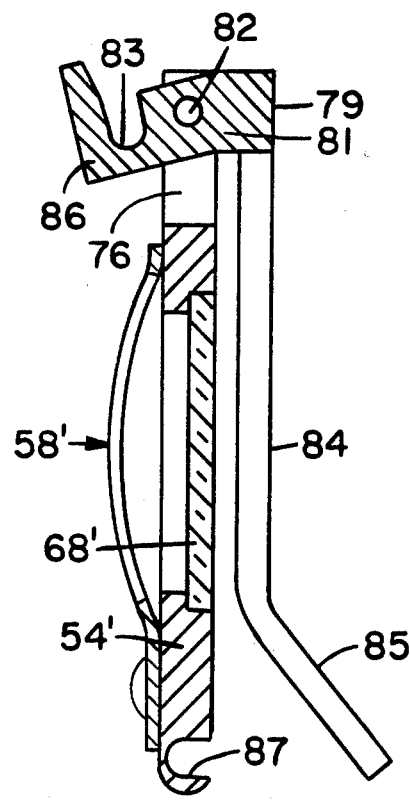
Fig. 5
Fig. 6
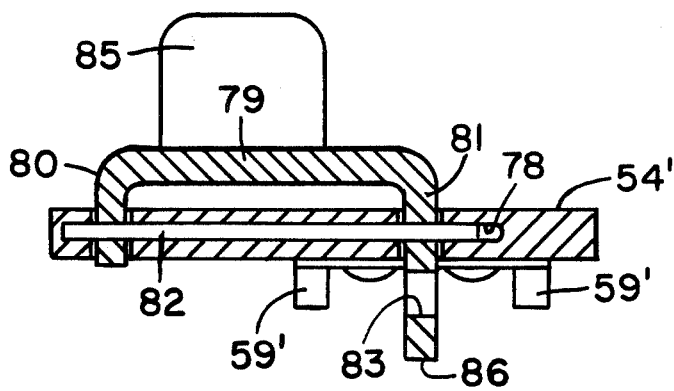
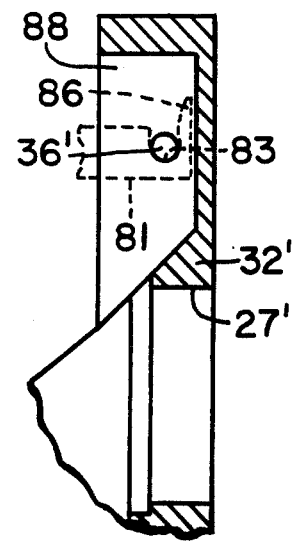
Fig. 7
Fig. 8

4,575,240

VISIBLE SAMPLE CHAMBER FOR FLUID ANALYSIS

BACKGROUND OF THE INVENTION

1. Field of the Invention

The present invention relates to instruments such as automatic blood analyzing instruments which rely upon the selective absorbance of light passing through a sample of thin cross-section. In such instruments the sample chamber is generally oriented perpendicular to the axis of the optical path. This places the sample chamber in an inaccessible location wherein, if any part thereof is visible, it is only one edge thereof. Therefore, various contaminants including small bubbles, clots and residue coatings, which may be present in the sample chamber and which drastically affect performance, cannot be identified. Sample chambers are also often difficult to disassemble for cleaning, and cleaning procedures often result in lengthy device shutdowns.

2. Description of the Prior Art

U.S. Pat. No. 4,134,678 teaches an instrument in which the sample cuvette is held perpendicular to the optical axis by a removable frame. In order to visually monitor a sample, the holding frame and cuvette must be removed from a temperature regulated zone, thereby necessitating a warm-up period after the cuvette is replaced in the instrument. When the cuvette holder is removed from the instrument it is mounted on a cuvette clip on the front plate of the instrument. A light source adjacent to the cuvette clip allows the operator to see whether there is a blood clot, impurity, bubble or other foreign substance in the cuvette.

U.S. Pat. No. 3,972,614 teaches a sample chamber which is situated within the housing of an ultrasonic hemolyzer. The sample chamber can be visually inspected only after, dismanteling the hemolyzing unit, whereby the instrument is subjected to a significant period of inoperability.

SUMMARY OF THE INVENTION

It is therefore an object of the present invention to provide a sample cuvette which is visible to the operator while it is in position for measurement in the instrument. Another object is to provide a fluid analyzing instrument in which the sample cuvette is readily disassembled for cleaning.

The present invention relates to an apparatus for analyzing a fluid. Such an apparatus conventionally comprises a sample chamber for supporting the fluid, means for directing a beam of light through the fluid, and means for analyzing the light emanating from the fluid. The sample chamber of the present invention is characterized in that it comprises a first member for forming a portion of the chamber, at least that portion of the first member which is located along the axis of the light beam being transparent. The first member has a flat surface which includes the transparent portion. A transparent prism is situated so that a first flat surface thereof is adjacent to the flat surface of the first member. Means is provided for supporting the flat surfaces of the first member and the prism in a spaced, substantially parallel relationship. A region between the first member and the prism is sealed to form a chamber through which the axis of the light beam passes. Means is provided for flowing the fluid through the chamber.

The apparatus also includes means for urging the first member and the prism toward each other.

BRIEF DESCRIPTION OF THE DRAWINGS

FIG. 5 is a view of the prism-facing surface of a prism-retaining door having a modified latching mechanism.

FIGS. 6 and 7 are cross-sectional views taken along lines 6—6 and 7—7, respectively, of FIG. 5.

FIG. 8 illustrates a modification of the housing which enables the use of the latching mechanism of FIGS. 5-7.

DESCRIPTION OF THE PREFERRED EMBODIMENT

Figure 1:
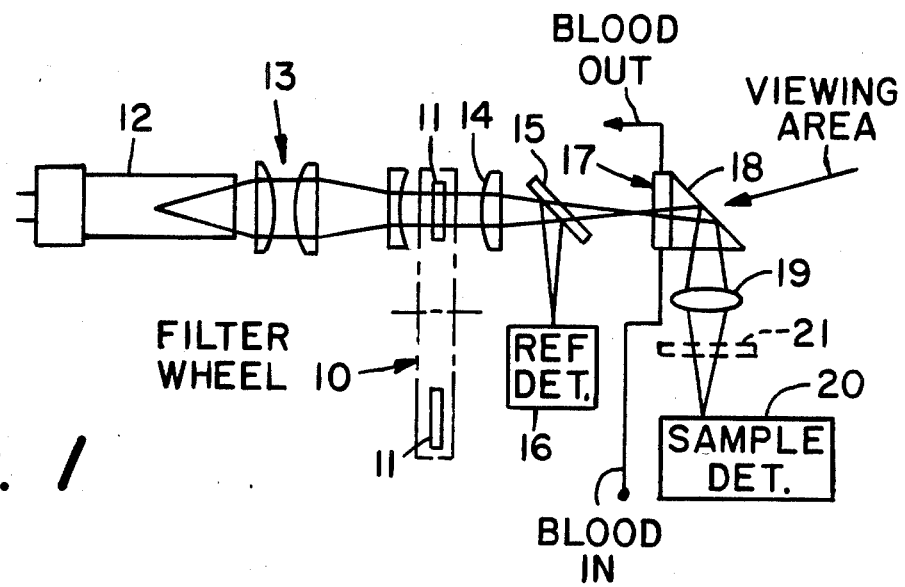
FIG. 1 is block diagram of the electro-optical system of the present invention.

The instrument of the present invention was designed specifically for the automatic analysis of blood. By determining the effect of a blood sample on different wavelengths of light, such measurements as hemoglobin, oxyhemoglobin, carboxyhemoglobin and methemoglobin fractions can be made and oxygen saturation can be calculated. However, the invention generally pertains to instruments in which a liquid sample is supported in a transparent cuvette through which a light beam passes.

The apparatus includes a filter wheel 10 having seven filters 11 around the periphery thereof. A hollow cathode tube 12 generates light having a plurality of selected wavelengths. The light is collimated by a lens system 13 and propagated through filter 11 and lens 14 to a beam splitter 15. A portion of the beam is reflected by beam splitter 15 to reference detector 16, and the remainder thereof is directed toward a sample chamber which is formed by a sample chamber assembly 17 which includes prism 18. The light beam as modified by the sample in the chamber is reflected by prism 18 and focussed by lens 19 onto sample detector 20. A filter 21 may optionally be employed in conjunction with one embodiment hereof. The various optical components such as lenses and prism are formed of conventional materials such as glass or plastic, glass being preferred.

Figure 2:
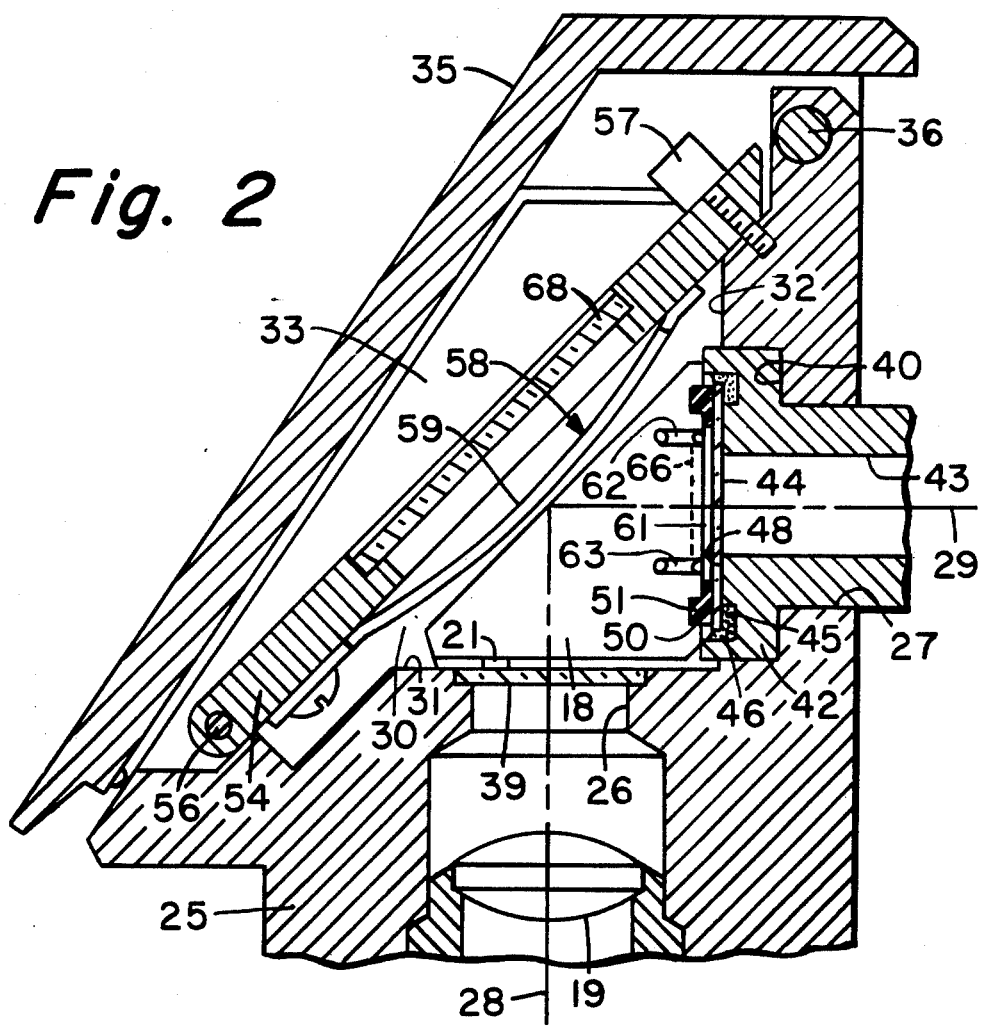
FIG. 2 is a cross-sectional view of that portion of the system which includes the sample chamber.
Figure 3:
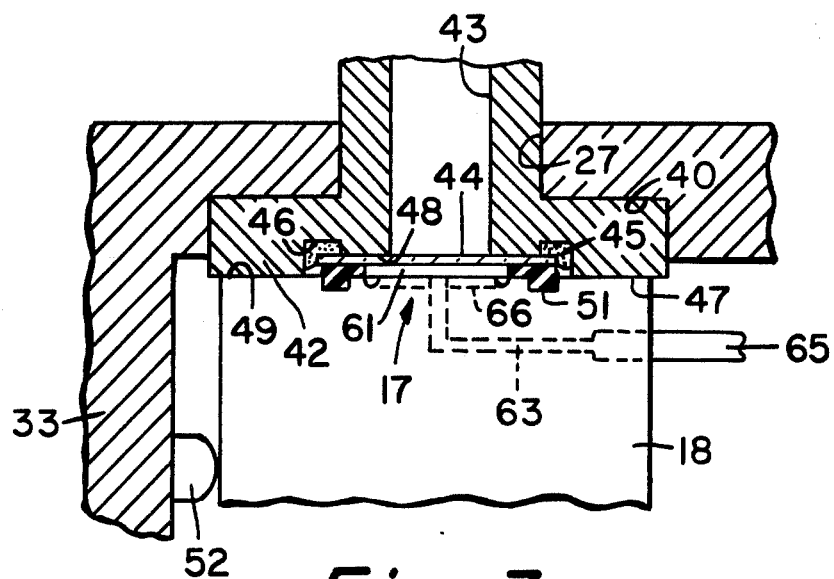
FIG. 3 is a partial cross-sectional view of the sample chamber of FIG. 2 taken along optical axis 29.
Figure 4:
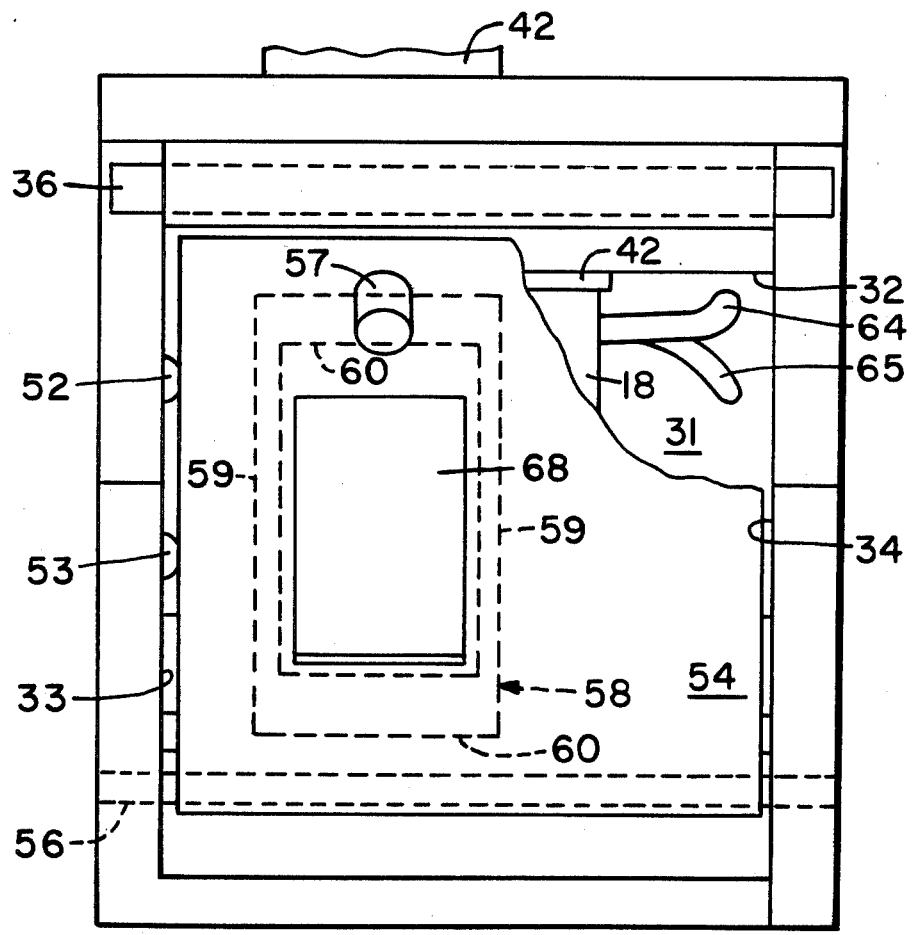
FIG. 4 is a top view of the apparatus of FIG. 2, door 35 having been removed and door 54 being partially broken away to reveal greater detail.

Sample chamber assembly 17 is shown in greater detail in FIGS. 2, 3 and 4. The components which comprise the sample chamber assembly are located in a housing 25 having orthogonally disposed bored 26 and 27 through which the optical axes 28 and 29 respectively extend. Light from the beam splitter 15 propagates along axis 29, reflects from the hypotenuse surface of prism 18, and propagates along axis 28, through lens 19 toward detector 20. Axes 28 and 29 intersect in a cavity 30 defined by a bottom surface 31, a rear wall 32 and two opposed sidewalls 33 and 34. A glass window 39 is mounted in an annular depression in surface 31 which is concentric with bore 26. the top surface of window 39 is coplanar with surface 31. A rectangularly shaped depression 40 in wall 32 surrounds bore 27.

Seated within depression 40 is a rectangularly-shaped member 42 which may be formed of stainless steel. Member 42 has an annular protrusion which extends through bore 27. Centrally located within member 42 is an annular bore 43. The surface of member 42 facing cavity 30 contains an annular groove 46 which separates a peripheral surface region 47 from an annular surface region 48. Surface region 48 is recessed about 7.7 mm from the plane of surface region 47. A circular window 44 formed of sapphire, glass or the like lies directly on surface region 48, the edge thereof extending over groove 46. The window is secured in position by bonding material 45. Since the thickness of window 44 is 7.6 mm, the surface thereof is recessed 0.1 mm from peripheral surface region 47.

Prism 18 forms the remaining portion of the sample chamber. Surface 49 of the prism contains an annular groove 50 that is concentric with optical axis 29. A gasket 51 of elastomeric material such as Viton, neoprene rubber or the like is disposed in groove 50. When prism 18 is properly situated within cavity 30, gasket 51 is compressed between the prism and window 44. Gasket 51 preferably comprises a relatively thick outer region which extends into groove 50 and a thinner region which extends radially inwardly from groove 50 between prism 18 and window 44, thus forming a sealed chamber 61 between the prism and window 44. Two small diameter holes 62 and 63 are drilled through the prism. Each hole comprises a short section which is perpendicular to surface 49 and a longer section which extends to a sidewall of the prism. Tubes 64 and 65, which project through openings in surface 31, are inserted into enlarged outer regions of holes 62 and 63, respectively. The points of emergence of holes 62 and 63 from prism 18 lie in a shallow annular channel 66. The innermost extension of gasket 51 stops just short of channel 66. In the preferred embodiment described herein, wherein blood samples are analyzed within the sample chamber, the diameter of the centerline of channel 66 was 0.4 inch. The channel was 0.01 inch deep and it had a 0.02 inch radius of curvature.

The novel subcombination of a sample chamber assembly formed of first and second transparent members having any suitable shape, means for supporting flat surfaces of the two members in spaced relationship, means for sealing off a region between the flat surfaces, and means for flowing fluid through the chamber, in combination with a channel such as annular channel 66, which extends around the periphery of the sample chamber formed between the two surfaces, was invented by another subsequent to the invention herein described and claimed. The annular groove in this subcombination provides improved flow of samples and cleaning fluids into and out of the sample chamber assembly 17, and improved drying of the sample chamber assembly 17 after cleaning and before introduction of a subsequent sample. The subcombination of a sample chamber provided with annular channel 66 is useful in a variety of applications and should not necessarily be limited to the shape of the prism 18.

Prism 18 is installed in cavity 30 in the following manner. Doors 35 and 54 are opened. The bottom surface of the prism rests on two chemical-resistant supports 21 which lift the prism above surface 31 and permit surface 49 of the prism to assume the proper vertical orientation relative to surface 47 of member 42. Prism 18 is urged toward sidewall 33 until it contacts stops 52 and 53. Prism-retaining door 54, which pivots on pin 56, is then closed and secured by tightening screw 57 into a threaded bore in rear wall 32. A retaining force is transmitted from door 54 to prism 18 by means such as a spring 58 which may be formed of stainless steel, beryllium-copper alloy or the like. As shown in dashed lines in FIG. 4, spring 58 comprises two curved portions 59 which are connected at their extremities by cross-members 60. The lower cross-member 60 is secured to door 54 by a pair of screws, the remaining cross-member being free to slide along the door. Curved portions 59 of the spring contact prism 18 on opposite sides of the point where optical axes 28 and 29 intersect at the hypotenuse face thereof. Other suitable resilient means such as metal bellows or a resilient gasket could be employed.

The force imparted by spring 58 upon prism 18 urges the prism toward member 42 and compresses gasket 51 until prism surface 49 contacts surface 47. In one embodiment, it was determined that the prism must be pressed against the sample chamber assembly with a force of at least 20 pounds if the sealing gasket is to be fully compressed and the 0.1 mm sample chamber thickness maintained. Since a 45° prism was employed, and very low friction existed between the prism and its supporting points, it was determined that the spring must exert a force of at least 28 pounds against the prism. In an alternative embodiment, the door could be spring loaded to enable direct contact between the door and prism.

During operation, a blood sample is taken up by the instrument, is hemolyzed, and thereafter flows through tube 65 and hole 63 to chamber 61. The sample flows through channel 66 and spreads across the 0.1 mm thick sample chamber 61. The overflow of blood flows outwardly through hole 62 and tube 64 where its presence can be ascertained by a suitable detector (not shown) which indicates that a sample is present within chamber 61.

In accordance with well known techniques, a light beam propagating along axis 29 passes through the sample. In the present instrument, the beam as modified by the sample reflects from the hypotenuse surface of prism 18 to form a reflected beam which propagates along axis 18 through window 39 and lens 19 which focuses it onto the sample detector.

As indicated hereinabove, it is desirable to identify contaminants including small bubbles and residue coatings which may be present in the sample chamber. The sample chamber described herein can be viewed through a window 68 located in door 54. Since measurements cannot be reliably made while ambient light enters the system, such light must be excluded at least during the time when the measurement is being made. One technique would be to utilize as window 68 a filter which would permit the passage of light at wavelengths other than those which are used to make the measurements. That light which passed through the filter window would be blocked out before it reached the detector by means of another filter 21 (see FIG. 1). Such an embodiment, however, also restricts the amount of light available for use by the operator to detect the contaminants or bubbles within the sample chamber.

In a preferred embodiment, window 68 is highly transparent to all visible light. Thus, ambient light at normal laboratory room intensities is allowed to flood the prism area. Under these conditions, any bubbles present larger than 0.1 mm in diameter appear silver against the red field of the blood and are highly visible. When employing such a transparent window 68, an opaque door 35, which pivots about pin 36, prevents ambient light from entering cavity 30 until it is raised. This embodiment, which employs an outer viewing door and an inner, prism-retaining door having a window transparent to visible light, provides excellent viewing of the sample under ordinary laboratory room light intensities.

The employment of a prism as one side of the sample chamber also enables the housing to be constructed so that the surfaces thereof which form cavity 30 are relatively free of surface irregularities, and the cavity is relatively open, thereby facilitating spill containment and cleaning. The sample chamber can be dismantled for contaminant removal by lifting viewing door 35 and releasing the restraint on the prism retaining door. After opening the latter door and removing tubes 64 and 65, prism 18 can be removed, and gaskets 51 can be taken from groove 50, if necessary. Both the prism and window 44 can be flushed with cleaning fluid.

The above-described system enables an operator to monitor the quality of an in-place sample at operational temperature prior to measurement, thereby ensuring reliable spectral analysis. Also, the present system can be quickly dismantled and cleaned, resulting in limited periods of instrument inoperability.

The invention may take forms other than that described above and is susceptible of various changes without departing from the principles thereof. For example, whereas the retaining mechanism for the prism-retaining door is illustrated in FIGS. 2 and 4 as being a screw, it could also be a latch mechanism of the type illustrated in FIGS. 5-7, wherein elements similar to those previously described are reprsented by primed reference numerals. In this embodiment door 54' is provided with a pair of slots 76 and 77 in the top thereof. A bore 78 parallel to the top surface of the door extends through the sidewalls of the slots. The latching mechanism comprises a cross-member 79 having flanges 80 and 81 at opposite ends thereof which extend into slots 77 and 76, respectively. A pin 82 extends through bore 78 and through bores extending through flanges 80 and 81 to secure the latching mechanism to door 54'. Flange 81, which is located along door 54' approximately midway between vertical sections 59' of the spring, contains an extension 86 which includes a slot 83. A handle 84 is attached to cross-member 79 and extends downwardly therefrom to an outwardly-projecting portion 85 which facilitates lifting.

As shown in FIG. 6, this embodiment contains a further modification whereby bore 87, which receives the door-retaining pin, extends to the outer surface of the door so that the entire door may be readily removed to facilitate removal of the prism and cleaning of the cavity.

Reference will be made to various portions of the housing of FIGS. 2 and 4 in order to describe the operation of the latch mechanism of FIGS. 5-7. To install and latch door 54', handle 84 is initially lifted away from the door, and open-faced bore 87 is placed over pin 56. To accommodate the door illustrated in FIGS. 5-7 the rear wall is modified as shown in FIG. 8 wherein elements similar to those shown in FIG. 2 are represented by primed reference numerals. Rear wall 32' is provided with a slot 88 in the vicinity of the bore which receives screw 57 of FIG. 2. Slot 88 exposes pin 36'. After door 54' is closed, handle 84 is pushed down to cause latching extrusion 86 of flange 81 to engage pin 36'. Further movement of the handle closes the door more tightly until pin 36' is seated at the bottom of slot 83.

Whereas the means for flowing the sample to and from chamber 61 have been described as being bores in prism 18, such means could instead comprise bores through member 42 and window 44. Annular channel 66 could be formed in the surface of window 44. Whereas gasket 51 is shown as being seated within groove 50, that gasket could instead be seated within a similar groove in the surface of window 44, provided that the window is of sufficient thickness.

We claim:

1. An apparatus for automatically analyzing a fluid comprising;
    a first transparent member having a flat surface,
    a transparent prism having a first flat surface adjacent to said flat surface of said first member,
    means for supporting said flat surfaces of said first member and said prism in a spaced, substantially parallel relationship,
    means for sealing off a region between said flat surfaces, the sealed-off region constituting a sample chamber for supporting said fluid,
    means for flowing said fluid through said chamber,
    means for urging said first member and said prism toward each other,
    means for directing a beam of light through said first transparent member and said first prism surface, said beam reflecting from a second surface of said prism and passing through a third surface of said prism,
    means for automatically analyzing the resultant light beam, and
    optical path means in said instrument adjacent said second surface of said prism for operator inspection of said sample chamber, whereby said sample chamber can be inspected through said prism.

2. An apparatus in accordance with claim 1 further comprising a door, and wherein said means for urging comprises a spring mounted on said door which, in its closed condition, positions said spring such that is bears against said second surface of said prism, said door having a transparent window which forms a part of said optical path means.

3. An apparatus in accordance with claim 2 wherein said window is transparent to light in the entire visible spectrum, said apparatus further comprising outer door means for preventing the transmission of light through said window when in the closed position.

4. An apparatus in accordance with claim 2 wherein said window filters light at certain wavelengths within the visible spectrum.

5. An apparatus in accordance with claim 1 wherein said means for flowing comprises first and second holes through said prism to said chamber.

* * * * *